United States Patent [19]

Barranx et al.

[11] Patent Number: 5,763,468

[45] Date of Patent: Jun. 9, 1998

[54] DISINFECTANT OR ANTISEPTIC COMPOSITION COMPRISING AT LEAST ONE TERPENE ALCOHOL AND AT LEAST ONE BACTERICIDAL ACIDIC SURFACTANT, AND USE OF SUCH A MIXTURE

[75] Inventors: Alain Barranx, Oeyreluy; Michel Barsacq, Dax; Ghislain Dufau, Dax; Jean-Paul Lauilhe, Dax, all of France

[73] Assignee: Action Pin, Dax, France

[21] Appl. No.: 682,769

[22] PCT Filed: Nov. 29, 1995

[86] PCT No.: PCT/FR95/01573

§ 371 Date: Oct. 10, 1996

§ 102(e) Date: Oct. 10, 1996

[87] PCT Pub. No.: WO96/16548

PCT Pub. Date: Jun. 6, 1996

[30] Foreign Application Priority Data

Nov. 30, 1994 [FR] France ................................. 94 14398

[51] Int. Cl.$^6$ .............................. A01N 65/00; A01N 57/12; A01N 37/36; A01N 31/04
[52] U.S. Cl. ...................... 510/383; 514/129; 514/557; 514/558; 514/559; 514/560; 514/568; 510/382

[58] Field of Search ...................... 510/382, 383

[56] References Cited

FOREIGN PATENT DOCUMENTS

| | | |
|---|---|---|
| A-1 153 267 | 9/1983 | Canada. |
| A-0 288 689 | 11/1988 | European Pat. Off.. |
| A-294 635 | 10/1991 | Germany. |
| A-42 25 626 | 2/1994 | Germany. |
| WO-A-81 01516 | 6/1981 | WIPO. |
| WO-A-89 01023 | 2/1989 | WIPO. |

*Primary Examiner*—John M. Ford
*Assistant Examiner*—Pavanram K. Sripada
*Attorney, Agent, or Firm*—Wenderoth, Lind & Ponack, L.L.P.

[57] ABSTRACT

A quaternary-ammonium-free composition having bactericidal activity for both Gram positive and Gram negative bacteria, and including (i) at least one terpene alcohol and (ii) at least one bactericidal acidic surfactant such as an alkyl polyether carboxylic acid, an alkenyl polyether carboxylic acid, an alkylaryl polyether carboxylic acid or a phosphoric ester of an alkoxylated non-ionic surfactant, particularly a phosphoric mono- or diester, in acidic or partially neutralized form.

15 Claims, No Drawings

DISINFECTANT OR ANTISEPTIC COMPOSITION COMPRISING AT LEAST ONE TERPENE ALCOHOL AND AT LEAST ONE BACTERICIDAL ACIDIC SURFACTANT, AND USE OF SUCH A MIXTURE

This application is a national phase application of International Application No. PCT/FR95/01573 filed Nov. 29, 1995.

The present invention relates to a disinfectant or antiseptic composition based on terpene alcohol and possessing broad-spectrum bactericidal activity, that is to say activity both on gram-positive and gram-negative bacteria.

The present invention relates to the bactericidal properties of terpene alcohols, in particular those present in essential oils or pine oil.

Pine oils consist of mixtures of terpene hydrocarbons and alcohols. In these mixtures, the proportions of terpene hydrocarbons and alcohols may be in a ratio of from 20/80 to 95/5, preferably 50/50 to 95/5. The terpene alcohols are essentially composed of monocyclic terpene alcohols (terpineols, terpin-1-en- 4-ol, etc.) and, in lower proportion, tricyclic terpene alcohols (fenchol, borneol, etc.).

Pine oil is known and used for its bactericidal properties in disinfectant compositions, in cleansing and disinfectant compositions and in antiseptic compositions. However, the bactericidal activity of such compositions is limited to gram-negative bacteria.

The reason for this is that terpene alcohols, in particular those of pine oil, in solution, in microemulsion or in aqueous dispersion, are not effective on gram-positive microorganisms, at the very least not in the forms currently available.

In order to obtain a disinfectant or antiseptic which has a broad spectrum of antibacterial efficacy, one or more compounds having bactericidal activity against gram-positive microorganisms thus have to be used in combination with the pine oil.

In a conventional manner, these bactericidal active materials are selected from quaternary ammoniums, phenol derivatives, aldehydes, etc. However, these compounds have the major drawback of being too dangerous at certain concentrations and are thus not sufficiently harmless towards the user.

To prepare disinfectant or antiseptic compositions with broad-spectrum efficacy which do not use such compounds, it would appear to be advantageous to study other combinations with terpene alcohols which afford the same properties.

The present inventors have discovered that the combination of certain surfactants, which themselves have bactericidal properties against gram-positive and gram-negative microorganisms, with a terpene alcohol makes it possible to achieve this aim in a noteworthy manner.

The subject of the present invention is thus a disinfectant or antiseptic composition which possesses bactericidal activity both on gram-positive and gram-negative bacteria, this composition containing no quaternary ammonium and comprising (i) at least one terpene alcohol and (ii) at least one bactericidal acidic surfactant such as, in particular, an alkyl polyether carboxylic acid, an alkenyl polyether carboxylic acid, an alkylaryl polyether carboxylic acid or a phosphoric ester of an alkoxylated nonionic surfactant, in acidic or partially neutralized form.

The present invention also provides broad-spectrum bactericidal, disinfectant, cleansing compositions comprising the ingredients mentioned above.

The composition according to the invention may advantageously comprise (i) a mixture of terpene alcohols containing, in particular, 30 to 100% by weight of monocyclic terpene alcohols, preferably 80 to 95%. It may in particular comprise a mixture containing 70 to 100% by weight of terpineols, preferably 80 to 90%.

The composition may also advantageously comprise (i) a mixture comprising at least one terpene alcohol and at least one terpene hydrocarbon.

Preferably, the weight proportions of terpene alcohol(s) and terpene hydrocarbon(s) are in a ratio of from 20/80 to 95/5, in particular 50/50 to 95/5.

In this case, pine oil may be used as mixture (i). The latter may be of natural or synthetic origin, obtained, for example, by catalytic hydration of α-pinene.

The other important component of the composition according to the invention is a bactericidal acidic surfactant (ii).

When the acidic surfactant (ii) is of alkyl, alkenyl or alkylaryl polyether carboxylic acid type, the polyether chain is advantageously of polyoxyethylene, polyoxypropylene or mixed polyether type derived from ethylene oxide and propylene oxide.

In particular, the surfactants of formula (A)

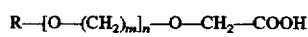

R—[O—(CH$_2$)$_m$]$_n$—O—CH$_2$—COOH in which R is chosen from a $C_4$–$C_{22}$ alkyl group, a $C_{18}$–$C_{22}$ alkenyl group and an alkylaryl group having a $C_6$–$C_{22}$ alkyl chain, m may be 2 or 3 and n is between 1 and 20, are preferred.

Surfactants of choice are polyoxyethylene carboxylic acids, that is to say compounds of formula (A) in which m is 2.

A $C_4$–$C_{22}$ alkyl group may be, in particular, a butyl, hexyl, octyl, decyl, lauryl, tridecyl, palmityl, stearyl, etc. group.

A $C_{18}$–$C_{22}$ alkenyl group may be, in particular, an oleyl, linoleyl, etc. group.

An alkylaryl group having a $C_6$–$C_{22}$ chain may be, in particular, an alkylphenyl group, in particular an octylphenyl or nonylphenyl group.

Such surfactants are, for example, certain Akypo® trademarks, marketed by the company Chemy, certain Sandopan® trademarks, marketed by the company Sandoz, certain Rewopol® trademarks, marketed by the company Witco, certain Marlinat® trademarks, marketed by the company Hüls, certain Empigen® trademarks, marketed by the company Albright & Wilson,, and certain Betadet® trademarks, marketed by the company Kao Corporation.

When the bactericidal acidic surfactant (ii) is of phosphoric ester of alkoxylated nonionic surfactant type, the nonionic surfactant may be, in particular, an ethoxylated, propoxylated or ethoxylated-propoxylated surfactant. The fundamental hydrocarbon chain of the surfactant may be of alkyl or alkylaryl type.

Mention may be made, by way of illustration, of phosphoric mono- or diesters, for example of the respective formulae (B) and (C):

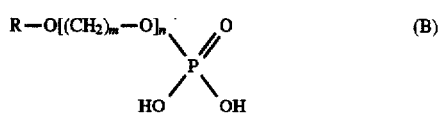

(B)

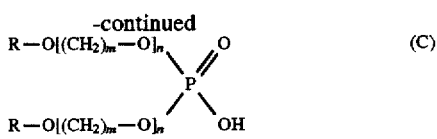

in which R is a $C_4$-$C_{20}$ alkyl group, m is 2 or 3 and n is between 1 and 20.

Examples of phosphoric esters which may be mentioned are certain Rhodafac® trademarks, marketed by the company Rhône-Poulenc.

The bactericidal acidic surfactants used may be present in the compositions of the invention exclusively in their acidic form, or in a partially neutralized form, that is to say in the form of an acidic surfactant/neutralized surfactant mixture.

Advantageously, the composition is in the form of an emulsifiable or dilutable concentrate, simply comprising the terpenic and surfactant active materials, or a dispersion, or a microemulsion or a solution in water of the active materials. Such an aqueous composition may be obtained in particular by dispersion, microemulsion or dilution in water of an emulsifiable or dilutable concentrate of active materials.

Preferably, the composition comprises (i) from 2 to 90%, in particular 5 to 90%, by weight of terpene alcohol(s), alone or as a mixture with one or more terpene hydrocarbon(s), and (ii) from 2 to 50%, in particular 5 to 50%, by weight of bactericidal acidic surfactant(s), the remainder optionally consisting (iii) of water in the case of an aqueous solution, microemulsion or dispersion.

A particularly preferred composition comprises (i) 5 to 20% by weight of at least one of the said terpene compounds, in particular pine oil, (ii) 5 to 20% by weight of bactericidal acidic surfactant(s), water representing the remainder.

The surfactants described above are used in the composition of the present invention not only on account of their bactericidal activity but also by virtue of their emulsifying or solubilizing role with respect to terpene compounds which are ordinarily water-insoluble.

In addition, at least one non-bactericidal surfactant may also be used as additive (iv) in order to improve the dispersion, microemulsion or solubilization of the terpene compounds in water.

Similarly, a solution, a microemulsion or an emulsion of terpene compound(s) in water to which bactericidal acidic surfactant(s) has(have) been added is advantageously prepared by adding to this mixture at least one co-solvent, (v), in particular a non-bactericidal co-solvent. The co-solvent may advantageously be an alcohol, in particular isopropanol or ethanol, or a glycol ether.

A non-bactericidal co-solvent (v) acts in the composition only as a solubilization or emulsification adjuvant, but does not display bactericidal properties at the dose to which it is brought by dilution of the disinfectant or antiseptic composition to the effective dose of the latter.

The amount of co-solvent (v) preferably represents 5 to 20% of the weight of the composition, more particularly about 10% of the weight of the composition.

Depending on the contents of terpene alcohol and of bactericidal acidic surfactant, the disinfectant or antiseptic compositions will be effective against gram-negative and gram-positive bacteria, in pure form or at low doses of use corresponding, for example, to dilution of the composition to less than 2% by volume in water.

An unexpected synergy effect is in particular observed between pine oil and the surfactants of polyether carboxylic acid type or of phosphoric ester of alkoxylated nonionic surfactant type. Indeed, the effective dose of a composition according to the invention containing a combination of the said ingredients is substantially less than the sum of the amounts of each active material, calculated on the basis of the efficacy of each active material taken individually, which are required in order to achieve the same result.

This synergy effect manifests itself in the activity against both gram-negative microorganisms and gram-positive microorganisms.

Reduction of the dose of disinfectants or antiseptics provided by the composition containing a synergic combination of bactericidal active materials according to the invention advantageously makes it possible to reduce the amount of wasted material associated with the use of the composition, in particular when this concerns cleansing-disinfectants.

The subject of the invention is thus also the use of a surfactant chosen from alkyl polyether carboxylic acids, alkenyl polyether carboxylic acids, alkylaryl polyether carboxylic acids and phosphoric esters of alkoxylated nonionic surfactants, in combination with at least one terpene alcohol, optionally as a mixture with at least one terpene hydrocarbon, as a bactericidal mixture in a disinfectant or antiseptic composition which possesses bactericidal activity against both gram-negative and gram-positive bacteria.

In addition, all the compositions based on terpene alcohol (s), alone or as a mixture with one (or more) terpene hydrocarbon(s), of the present invention have the major advantage of conserving their bactericidal efficacy against all types of organism under severe conditions of use. Thus, the compositions of the invention remain effective when they are used in the presence of interfering substances, for example with hard water, or for cleaning a surface soiled with organic materials, in particular proteins. In contrast with the use with conventional cleansing-disinfectants, it is not necessary to increase the dose of active material considerably in order to obtain satisfactory disinfection in interfering media.

This noteworthy and surprising efficacy, which is characteristic of the compositions according to the present invention, will now be demonstrated in the examples which follow.

EXAMPLE 1

A cleansing solution is prepared from pine oil and lauryl polyoxyethylene carboxylic acid in accordance with the invention.

Lauryl polyoxyethylene carboxylic acid is a bactericidal surfactant which is active against gram-negative and gram-positive bacteria.

Its bactericidal efficacy may be measured in accordance with AFNOR Standard NFT 72-151.

Two bacterial strains are selected among the AFNOR strains as being representative of gram-positive and gram-negative bacteria which are usually resistant to disinfectants.

For the gram-negative bacteria, *Pseudomonas aeruginosa* is selected, which is known for its resistance in tests on disinfectants (strain CIP A22—Institut Pasteur).

For the gram-positive bacteria, *Enterococcus hirae* is selected for the same reasons (strain CIP 5855—Institut Pasteur).

For the purposes of the test, these strains are maintained according to AFNOR Standard NFT 72-140.

The bactericidal efficacy of the surfactant, expressed by the minimum concentration of active material of the said surfactant which kills the bacteria in the sense of the AFNOR test NFT 72-151, is reported in Table 1 below.

TABLE 1

|  | Efficacy on gram- bacteria (*Pseudomonas aeruginosa*) | Efficacy on gram+ bacteria (*Enterococcus hirae*) |
|---|---|---|
| Minimum concentration of laurylpolyoxyethylene carboxylic acid (expressed to 100% of active material) | 0.8% (8000 ppm of bactericidal active agent) | 0.8% (8000 ppm of bactericidal active agent) |

The formulation of the cleansing composition is as follows (the percentages being expressed as % by weight of active material):
Lauryl polyoxyethylene carboxylic acid 20%
Pine oil 20%
Isopropanol 10%
Water 50%.

The lauryl polyoxyethylene carboxylic acid used is a product marketed under the brand name Marlinat® CM 100 by the company Hüls. The formula of this surfactant is:

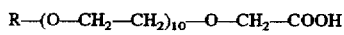

$$R-(O-CH_2-CH_2)_{10}-O-CH_2-COOH$$

where R is a lauryl group.

The pine oil used is a product marketed under the brand name Dertol® 90 by the company Les Dérivés Résiniques et Terpéniques, which comprises a mixture of terpenic alcohols and terpenic hydrocarbons whose terpenic alcohol content is between 88 and 93%.

The ingredients are mixed together until a stable microemulsion is obtained.

The bactericidal efficacy of the composition of Example 1 is also measured according to Standard NFT 72-151.

The result of the test is reported in Table 2, in which the efficacy of the composition is expressed by the maximum dilution (by volume), of the composition in distilled water, which makes it possible to kill the bacteria in the sense of the AFNOR test NFT 72-151.

In each case, the amount of bactericidal active agent corresponding to this dilution is given in the table. For the tests on gram-negative bacteria, the amount of bactericidal active agent corresponds to the total amount of pine oil and of surfactant (which each have an activity against bacteria of this type). For the tests on gram-positive bacteria, only the surfactant is taken into account as bactericidal active agent, the pine oil alone having no activity against bacteria of this type.

The composition is also subjected to a test to determine the bactericidal efficacy on gram-negative bacteria in the presence of hard water (60° TH) and in the presence of proteins according to the technical procedure of AFNOR Standard NFT 72-171. The results of this test are featured in Table 3.

COMPARATIVE EXAMPLE 1a

A composition containing no pine oil, but which contains the same amount of bactericidal acidic surfactant (lauryl polyoxyethylene carboxylic acid) as the composition of Example 1, is prepared and subjected to the AFNOR test NFT 72-151 as in Example 1.

The formulation is as follows (the percentages being expressed as % by weight of active material):
Lauryl polyoxyethylene carboxylic acid 20%
Isopropanol 10%
Water 70%.

The results of the test to determine the bactericidal efficacy are reported in Table 2.

COMPARATIVE EXAMPLE 1b

A composition containing no bactericidal acidic surfactant, but which contains the same amount of pine oil as the composition of Example 1, is prepared and subjected to the AFNOR test NFT 72-151 as in Example 1.

A surfactant is, however, needed to prepare the emulsion. A tall-oil sodium fatty acid soap which has no bactericidal properties is used.

The formulation is as follows (the percentages being expressed as % by weight of active material):
Pine oil 20%
Tall-oil sodium fatty acid soap 20%
Isopropanol 10%
Water 50%.

The results of the test to determine the bacterial efficacy are presented in Table 2.

EXAMPLE 2

Another composition corresponding to the following formulation is prepared from the ingredients of the composition of Example 1, and is subjected to the AFNOR test NFT 72-151
Lauryl polyoxyethylene carboxylic acid 20%
Pine oil 5%
Isopropanol 10%
Water 65%.

The results of the test to determine the bactericidal efficacy are presented in Table 2.

TABLE 2

| Composition | Efficacy on gram- bacteria (*Pseudomonas aeruginosa*) | Efficacy on gram+ bacteria (*Enterococcus hirae*) |
|---|---|---|
| Example 1 | 0.5% 2000 ppm of total bactericidal active agent | 0.5% 1000 ppm of bactericidal active agent |
| Example 2 | 1% 2500 ppm of total bactericidal active agent | 1% 2000 ppm of bactericidal active agent |
| Comparative Example 1a | 4% 8000 ppm of bactericidal active agent | 4% 8000 ppm of bactericidal active agent |
| Comparative Example 1b | 2% 4000 ppm of bactericidal active agent | inactive no bactericidal active agent |

The compositions of Examples 1 and 2 are effective at low doses of use.

The comparative examples demonstrate the synergistic effect between pine oil and the surfactant.

Thus, the addition of pine oil, which is inactive against gram-positive bacteria, to the surfactant, makes it possible to reduce by a factor of 8 the dose of bactericidal surfactant required for bactericidal activity against the gram-positive microorganisms.

Moreover, if the bactericidal properties of pine oil and the surfactant were simply additive, a mixture of 20% of each of them, according to Examples 1a and 1b, would not be effective on gram-negative bacteria at a dose of less than 6000 ppm of total bactericidal active agent. On the contrary, the composition of Example 1 remains effective down to a dose of 2000 ppm of total bactericidal active agent.

TABLE 3

| Composition of Example 1 | Efficacy on gram- bacteria (Pseudomonas aeruginosa) |
|---|---|
| Hard water (60° TH) | 1% |
| Proteins (1% albumin + 1% yeast extract) | 3% |

The composition of Example 1 is very effective under conditions of use in interfering media.

EXAMPLE 3

This example relates to the determination of the bactericidal efficacy of ethoxylated nonionic surfactants of phosphoric ester type.

As in Example 1, such surfactants are subjected to the AFNOR test NFT 72-151.

Two examples of these surfactants are as follows: Rhodafac® RA-600, which comprises a mixture of phosphoric mono- and diester of a $C_8$–$C_{10}$ alcohol ethoxylated with 6 mol of ethylene oxide, Rhodafac® RE-610, which comprises a mixture of phosphoric mono- and diester of ethoxylated nonylphenol, these products being marketed by the company Rhône-Poulenc.

The results of the tests to determine the bactericidal efficacy are presented in Table 4 below, expressed, as in Table 1, as the minimum concentration of active material of the said surfactant which kills the bacteria in the sense of the AFNOR test NFT 72-151.

TABLE 4

| Minimum concentrations of phosphoric esters (expressed to 100% of active materials) | Efficacy on gram- bacteria (Pseudomonas aeruginosa) | Efficacy on gram+ bacteria (Enterococcus hirae) |
|---|---|---|
| Active material of Rhodafac ® RA 600 | 0.04% (400 ppm) | 0.04% (400 ppm) |
| Active material of Rhodafac ® RE 610 | 0.2% (2000 ppm) | 0.4% (4000 ppm) |

These surfactants may be incorporated into disinfectant cleansing compositions similar to those of Examples 1 and 2.

EXAMPLE 4

A disinfectant cleansing composition is prepared from pine oil (Dertol® 90) and the mixture of phosphoric mono- and diester of ethoxylated nonylphenol, Rhodafac® RE-610.

The formulation of the disinfectant cleansing composition is as follows (the percentages being expressed as % by weight of active material):
Rhodafac® RE-610 20%
Pine oil 20%
Isopropanol 10%
Water 50%.

The ingredients are mixed together until a stable microemulsion is obtained.

The bactericidal efficacy of this composition is measured according to Standard NFT 72-151, on gram-negative bacteria.

The result of the test is reported in Table 5, in which the efficacy of the composition is expressed as the maximum dilution (by volume) of the composition in distilled water, which makes it possible to kill the bacteria in the sense of the AFNOR test NFT 72-151.

COMPARATIVE EXAMPLE 4a

A composition containing no pine oil, but which contains the same amount of bactericidal acidic surfactant as the composition of Example 4, is prepared and subjected to the AFNOR test NFT 72-151 as in Example 4.

The formulation is as follows (the percentages being expressed as % by weight of active material):
Rhodafac® RE-610 20%
Isopropanol 10%
Water 70%

The results of the test to determine the bactericidal efficacy are reported in Table 5, which also gives the results of Comparative Example 1b, corresponding to a composition free of bactericidal surfactant.

TABLE 5

| Composition | Efficacy on gram- bacteria (Pseudomonas aeruginosa) |
|---|---|
| Example 4 | 0.4% |
| | 1600 ppm of total bactericidal active agent |
| Comparative Example 4a | 1% |
| | 2000 ppm of bactericidal active agent |
| Comparative Example 1b | 2% |
| | 4000 ppm of bactericidal active agent |

The composition of Example 4 is also effective at a low dose of use.

The comparative examples demonstrate the synergistic effect between pine oil and the surfactant.

Thus, if the bactericidal properties of pine oil and the surfactant were simply additive, a mixture of 20% of each of them, according to Examples 4a and 1b, would not be effective on gram-negative bacteria at a dose of less than 3000 ppm of total bactericidal active agent. On the contrary, the composition of Example 4 remains effective down to a dose of 1600 ppm of total bactericidal active agent.

We claim:

1. A disinfectant or antiseptic cleansing composition which possesses bactericidal activity both on gram-positive and gram-negative bacteria, said composition being free of quaternary ammonium compounds and comprising
   (i) at least one terpene alcohol and
   (ii) at least one bactericidal acidic surfactant selected from alkyl polyether carboxylic acids, alkenyl polyether carboxylic acids, alkylaryl polyether carboxylic acids and phosphoric esters of an alkoxylated nonionic surfactant in acidic or partially neutralized form.

2. A composition according to claim 1, comprising
   (i) a mixture of terpene alcohols containing from 30 to 100% by weight of monocyclic terpene alcohols.

3. A composition according to claim 1, further comprising at least one terpene hydrocarbon.

4. A composition according to claim 1, further comprising at least one terpene hydrocarbon wherein the weight ratio of terpene alcohol(s) and terpene hydrocarbon(s) is in the range from 20/80 to 95/5.

5. A composition according to claim 1, further comprising at least one terpene hydrocarbon provided by pine oil.

6. A disinfectant or antiseptic cleansing composition which possesses bactericidal activity both on gram-positive and gram-negative bacteria, said composition being free of quaternary ammonium compounds and comprising
(i) at least one terpene alcohol and
(ii) at least one bactericidal acidic surfactant in acidic or partially neutralized form of formula (A):

R—[O—(CH$_2$)$_m$]$_n$—O—CH$_2$—COOH wherein

R is selected from a C$_4$–C$_{22}$ alkyl group, a C$_{18}$–C$_{22}$ alkenyl group and an alklaryl group having a C$_6$–C$_{22}$ alkyl chain, m is 2 or 3 and n is between 1 and 20.

7. A disinfectant or antiseptic cleansing composition which possesses bactericidal activity both on gram-positive and gram-negative bacteria, said composition being free of quaternary ammonium compounds and comprising
(i) at least one terpene alcohol and
(ii) at least one bactericidal acidic surfactant in acidic or partially neutralized form of formulae (B) and (C),

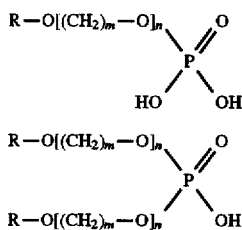

wherein

R is a C$_4$–C$_{20}$ alkyl group, m is 2 or 3 and n is an integer between 1 and 20.

8. A composition according to claim 7, comprising
(ii) a surfactant selected from phosphoric esters of ethoxylated, propoxylated and ethoxylated-propoxylated nonionic surfactants.

9. A disinfectant or antiseptic cleansing composition which possesses bactericidal activity both on gram-positive and gram-negative bacteria, said composition being free of quaternary ammonium compounds and comprising (i) from 2 to 90% by weight of at least one terpene alcohol or of a mixture of at least one terpene alcohol with at least one terpene hydrocarbon, (ii) from 2 to 50% by weight of a bactericidal acidic surfactant in acidic or partially neutralized form selected from alkyl polyether carboxylic acids, alkenyl polyether carboxylic acids, alkylaryl polyether carboxylic acids and phosphoric esters of an alkoxylated nonionic surfactant, (iii) the balance being water.

10. A composition according to claim 9, comprising (i) 5 to 20% by weight of a mixture of terpene alcohols and terpene hydrocarbons provided by pine oil, (ii) 5 to 20% by weight of said bactericidal acidic surfactant, (iii) the balance being water.

11. A composition according to claim 1, further comprising (iv) at least one non-bactericidal surfactant.

12. A composition according to claim 1, further comprising (v) a non-bactericidal co-solvent.

13. A composition according to claim 1, further comprising (v) a non-bactericidal co-solvent selected from an alcohol and a glycol ether.

14. A composition according to claim 1, further comprising (v) a non-bactericidal co-solvent in an amount from 5 to 20% by weight based on the weight of the composition.

15. A composition according to claim 1, further comprising (v) a non-bactericidal co-solvent selected from isopropanol and ethanol.

* * * * *

UNITED STATES PATENT AND TRADEMARK OFFICE
CERTIFICATE OF CORRECTION

PATENT NO. : 5,763,468
DATED : June 9, 1998
INVENTOR(S) : Alain Barranx et al.

It is certified that error appears in the above-indentified patent and that said Letters Patent is hereby corrected as shown below:

On the title page: item [75], correct the spelling of the last name of the second inventor to --Barsaco--; and item [86], correct both the §371 Date and the §102(e) Date to --September 10, 1996--.

Signed and Sealed this

Seventh Day of December, 1999

Attest:

Q. TODD DICKINSON

*Attesting Officer*     Acting Commissioner of Patents and Trademarks